United States Patent [19]
Hwang

[11] Patent Number: 5,005,589
[45] Date of Patent: Apr. 9, 1991

[54] CONDOM

[76] Inventor: Ying-Teh Hwang, No. 220, Ruey Feng Street, Kaohsiung, Taiwan

[21] Appl. No.: 497,610

[22] Filed: Mar. 22, 1990

[51] Int. Cl.[5] ............... A61F 6/04; A61F 5/44
[52] U.S. Cl. .................... 128/844; 128/918; 604/347
[58] Field of Search ........... 128/842, 844, 79, 918; 604/330, 347–353

[56] References Cited

U.S. PATENT DOCUMENTS

| | | | |
|---|---|---|---|
| 2,061,384 | 11/1936 | Manegold | 604/330 |
| 2,326,159 | 8/1943 | Mendel | 604/349 |
| 2,358,440 | 9/1944 | Bowman | 604/349 |
| 2,410,460 | 11/1946 | Robinson | 604/349 |
| 3,037,508 | 6/1962 | Friedman | 604/330 |
| 4,074,712 | 2/1978 | Wright | 604/349 |
| 4,840,188 | 6/1989 | Heidenfelder | 604/349 |
| 4,846,197 | 7/1989 | Benjamin | 604/353 |
| 4,898,184 | 2/1990 | Skurkovich | 604/349 |

FOREIGN PATENT DOCUMENTS

| | | | |
|---|---|---|---|
| 0275647 | 7/1988 | European Pat. Off. | 604/349 |
| 0039216 | 10/1909 | Fed. Rep. of Germany | 604/349 |
| 0111720 | 12/1928 | Fed. Rep. of Germany | 604/349 |
| 0146306 | 6/1936 | Fed. Rep. of Germany | 604/349 |
| 0676531 | 2/1930 | France | 128/844 |
| 0096564 | 10/1922 | Switzerland | 604/349 |
| 1252255 | 11/1971 | United Kingdom | 128/844 |

Primary Examiner—Robert A. Hafer
Assistant Examiner—Michael Brown
Attorney, Agent, or Firm—Bacon & Thomas

[57] ABSTRACT

A condom has a body, a sperm cell extending forward from the body and a vertical narrow flat neck between the body and the cell for the sperm to pass through in the cell. The sperm cell has an oval shape, the lower portion larger than the upper portion and the height is longer than the neck so that the sperm entering the cell may stay in the lower portion without few possibility to return through the neck to the body. Besides, a groove is provided at the front bottom of the body, conforming to the male sex organ.

5 Claims, 3 Drawing Sheets

A-A'

B-B'

C-C'

CONDOM

BACKGROUND OF THE INVENTION

Conventional condoms, as shown in FIGS. 1 and 2, comprises a body 11, a sperm cell 12 and a circumferential recess 13 in the front portion. The circumferential recess 13 surrounds just the recessed edge under the glans and the sperm cell 12 extends forward in front of the sperm shooting opening when the conventional condom is worn on a penis. This kind of conventional condom is considered to have the following disadvantages.

1. The sperm cell 12 is shaped as a bowl but the connecting point with the body 11 forms a passage of the same diameter as the cell 12 so that the sperm shot therein is quite easy to flow back to the glans and further to the body 11 around the penis. When the erecting penis shrinks after sperm shooting, the chance is that the shot-out sperm may flow out of the sperm cell and along the body 11 and finally out of the opening of the condom to cause conception, or that the condom may break accidentially to permit shot-out sperm leak out of it to the result of potential conception. Besides, the penis has to be washed clean if it is coated around the shot-out sperm flowing back in the body 11.

2. Air may be forced in the vagina by the action in the intercourse process, and if the forced-in air is not exhausted out to balance the inner and the outer pressure, the intercourse may not be smoothly carried on and both persons may feel unpleasant. It is natural that a woman gives out secretion fluid during the intercourse to keep her vagina wet enough for smoothing the action, and the circumferential recess under the glans serves for air ventilation and exhaustion of secretion fluid. As a conventional condom has its body 11 formed cylindrical to have the same diameter from the top to the bottom, it can not be useful for air ventilation and exhaustion of secretion fluid when it is worn on the penis, because the circumferential recess under the glans can be blocked. Sometimes the condom may contain some air if a user is too hasty in wearing it, and the circumferential recess may lose its function such that the intercourse cannot go smoothly enough to get satisfaction or some harm may occur if worse. And the outer and the inner pressure do not balance so that the condom receives bigger friction than otherwise, and thereby its breaking opportunity largely increases to the result of lessening contraception effectiveness. The cause is the loss of the functions for air ventilation and exhaustion of the secretion fluid that the circumferential recess should have.

This invention has been devised to improve the above-mentioned disadvantages of conventional condoms.

SUMMARY OF THE INVENTION

The condom in accordance with the present invention has a special structure that a vertical narrow flat neck is provided between the body and the sperm cell so that once the shot-out sperm enters the sperm cell through the neck can hardly flow back through the neck in the body.

One of the other different structure this condom has is that of the sperm cell for storing the sperm shot-out. The sperm cell extending forward from the body has a longer vertical height than that of the neck and the lower portion larger than the upper portion, therefore the sperm shot-out and entering the sperm cell through the neck flows along the inner surface down to the lower portion and gradually loses moving force to stay there without little possibility to flow back through the neck.

Besides, this condom is provided with a lengthwise groove at the front bottom of the body to conform to the shape of a male sex organ to enable it to function as a means for air ventilation and exhaustion of secretion fluid so that the action of intercourse can go smoothly, naturally and satisfactorily.

DETAILED DESCRIPTION OF THE INVENTION

Figure 1:
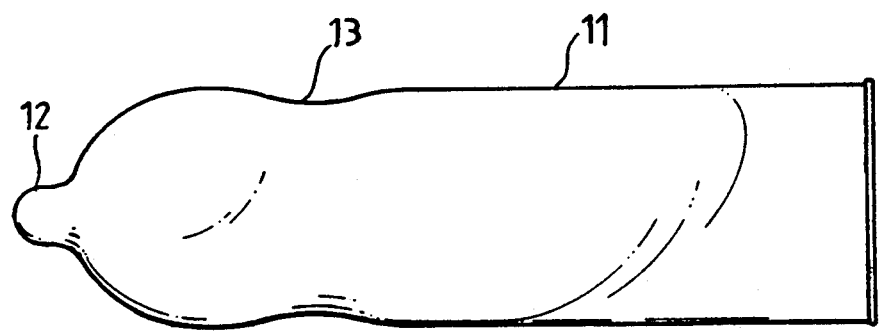
FIG. 1. is a perspective view of a conventional condom.
Figure 2:
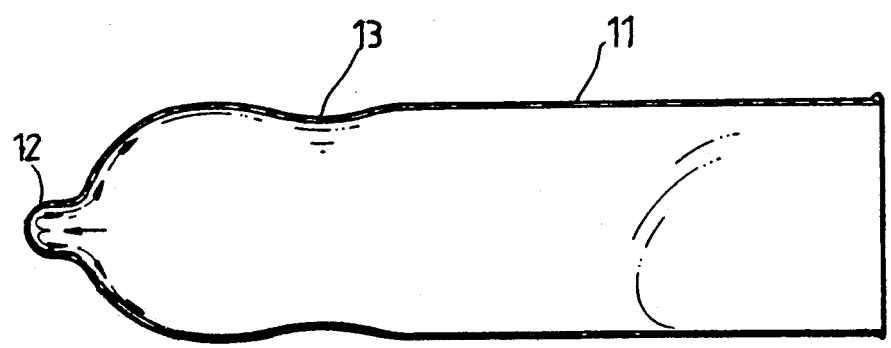
FIG. 2. is a cross-sectional view of a conventional condom.
Figure 3:
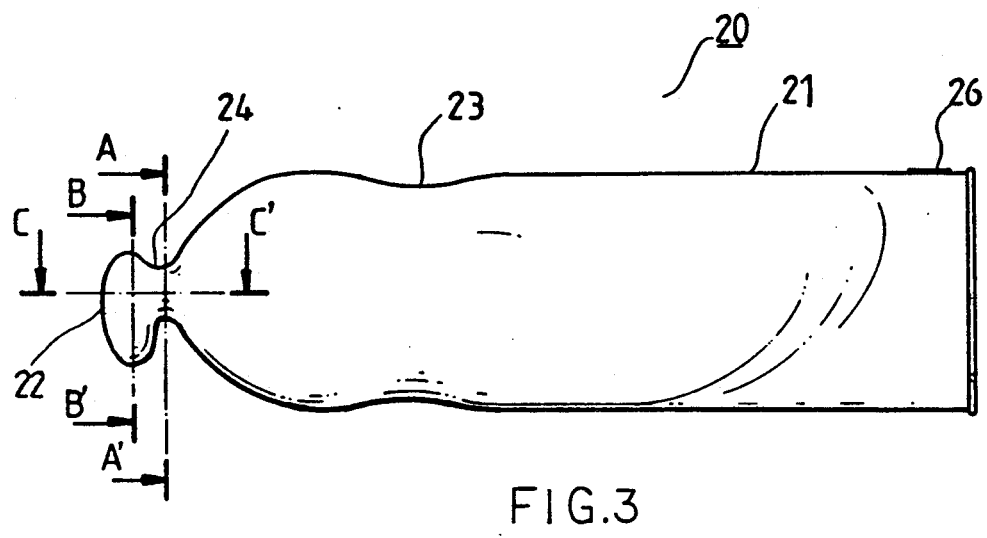
FIG. 3. is a perspective view of the condom in the present invention.
Figure 4:
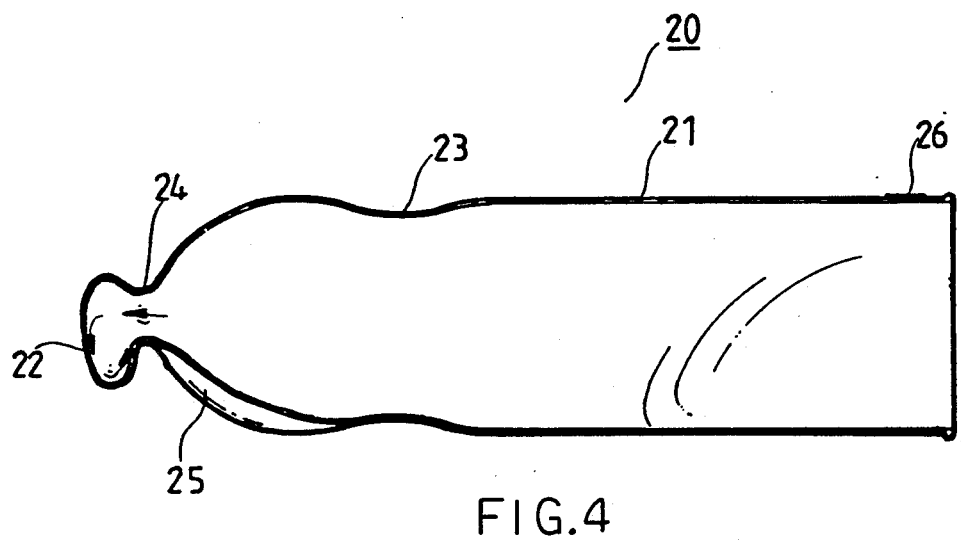
FIG. 4. is a cross-sectional view of the condom in the present invention.
Figure 5:
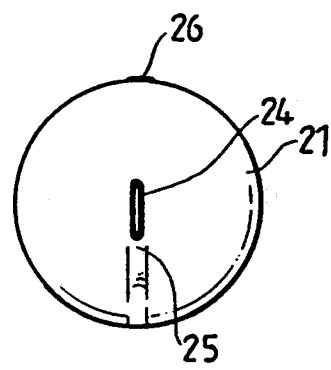
FIG. 5. is a cross-sectional view of A—A line on FIG. 3.
Figure 6:
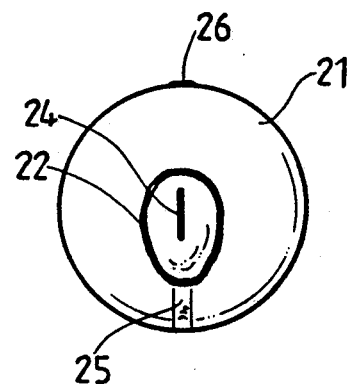
FIG. 6. is a cross-sectional view of B—B line on FIG. 3.
Figure 7:
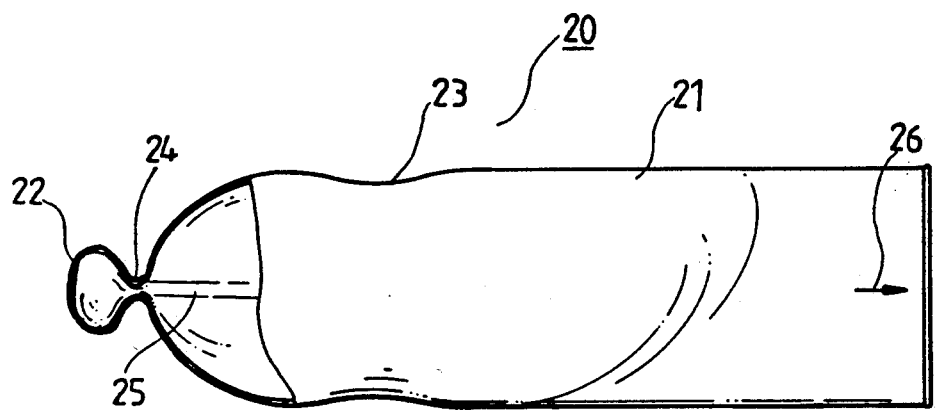
FIG. 7. is a cross-sectional view of C—C line on FIG. 3.

The condom in the present invention, as shown in FIGS. 3 and 4, comprises a body 21, a sperm cell 22, a circumferential recess 23 in the front portion and a neck 24 between the body 21 and the sperm cell 22. The neck 24 is vertical, narrow, flat and shorter in height than the sperm cell 22 to conform to the sperm shooting opening of a penis as shown in FIGS. 5, 6 and 7. The sperm cell 22 is shaped like an oval, quite different from that in a conventional one, and longer in height than the neck 24, having its lower portion bigger than the upper portion and its whole dimension properly made not to hamper intercourse. The shot-out sperm entering the cell 22 can flow along the inner surface down to the lower portion to stay there, hardly possible to flow back in the body 21 hindered by the narrow neck 24. Therefore, it may never happen that the sperm stored in the cell 22 runs out of the opening of the condom 20, to the result of real contraceptive effectiveness.

Referring to FIGS. 4 and 5, the body 21 is provided with a groove 25 at the front bottom extending lengthwise and correspondingly conforming to the groove in the penis so that the groove 25 can fit in the groove in the penis when this condom is worn thereon. Therefore, the groove 25 still has the same function as the groove in the penis for air ventilation and exhaustion of the secretion fluid, enabling intercourse smooth, natural and satisfactory. Besides, the contraceptive purpose can be completely attained because of very few possibility in breaking this condom, which receives little pressure owing to the balanced inner and outer pressure.

In order to use this condom in the correct position on the penis, with the neck 24 facing the sperm shooting opening, and the groove 25 fitting in the groove at the glans bottom, a colored mark 26 such as arrow-head can be made on the upper surface of the body 21 so that a user can at once know where the upper of this condom is in using it correctly. However, this condom can still function as a contraceptive means, even if it is worn in a slightly incorrect position.

What is claimed is:

1. A condom comprising:
   (a) an elongated body having a generally concavo-convex front portion and defining an interior space;
   (b) a sperm cell having a generally oval shaped cross-sectional configuration with a width and a height, the cross-sectional configuration taken in a plane extending generally perpendicular to the elongated body; and,
   (c) a neck portion connecting the sperm cell to the front portion of the elongated body, a slit extending from said neck portion into said elongated body, said slit having a width and height, the slit allowing communication between the interior space of the elongated body and the sperm cell wherein the width of the slit is substantially smaller than its height, and wherein the width and height of the slit are substantially smaller than the width and height of the sperm cell.

2. The condom as claimed in claim 1 wherein the oval shaped sperm cell has a larger portion of its height below the neck portion than above the neck portion such that the sperm shot into the cell may flow along an inner surface to the lower portion where the sperm is trapped.

3. The condom as claimed in claim 1 wherein the elongated body defines a lengthwise groove in a bottom of the front portion to conform to the shape of a male sex organ so as to have the function of air ventilation and exhaustion of the secretion fluid during the action of intercourse, such that the groove does not communicate with the interior space of the elongated body.

4. The condom as claimed in claim 1 wherein the elongated body has a mark on an upper surface for a user to know the correct position in using this condom.

5. The condom as claimed in claim 4 wherein the mark has a color different from that of the elongated body.

* * * * *